US007014870B1

(12) United States Patent
Hon et al.

(10) Patent No.: US 7,014,870 B1
(45) Date of Patent: Mar. 21, 2006

(54) COMPOSITIONS OF OAK BARK EXTRACT RELATED SYNTHETIC COMPOSITIONS AND METHOD OF USING SAME

(75) Inventors: David N.-S Hon, Clemson, SC (US); R. Thomas Stanley, Auburndale, FL (US)

(73) Assignee: Greystone Medical Group, Inc., Memphis, TN (US)

( * ) Notice: Subject to any disclaimer, the term of this patent is extended or adjusted under 35 U.S.C. 154(b) by 162 days.

(21) Appl. No.: 09/716,890

(22) Filed: Nov. 20, 2000

Related U.S. Application Data

(63) Continuation of application No. 08/947,055, filed on Oct. 8, 1997, now Pat. No. 6,149,947, which is a continuation of application No. 08/596,689, filed on Feb. 2, 1996, now abandoned, which is a continuation of application No. 08/334,795, filed on Nov. 4, 1994, now abandoned, which is a continuation of application No. 07/973,071, filed on Nov. 6, 1992, now abandoned.

(51) Int. Cl.
*A61K 33/00* (2006.01)
*A61K 33/06* (2006.01)
*A61K 33/30* (2006.01)
*A61K 33/14* (2006.01)

(52) U.S. Cl. ........................ 424/641; 424/642; 424/682
(58) Field of Classification Search ............. 424/195.1, 424/725, 771, 779, 641, 642, 682; 514/783
See application file for complete search history.

(56) References Cited

U.S. PATENT DOCUMENTS 5,080,900 A * 1/1992 Stanley .................... 424/195.1
6,149,947 A * 11/2000 Hon et al. .................. 424/641

* cited by examiner

*Primary Examiner*—Patricia Leith
(74) *Attorney, Agent, or Firm*—O'Melveny & Myers LLP

(57) ABSTRACT

Higher concentrations of oak bark ash extract, i.e., greater than 20% by weight, are useful for the treatment of skin cancers. Lower concentrations of oak bark extract possess additional therapeutic properties not heretofore recognized. For example, preparations containing 40–80% oak bark extract are useful in the treatment of acute cancerous skin ulcers. In addition, synthetic mixtures containing potassium ions, zinc ions, calcium ions provide many of the same advantageous properties of oak bark extract. The inclusion of rubidium ions and sulfur is also advantageous for some applications.

3 Claims, No Drawings

COMPOSITIONS OF OAK BARK EXTRACT RELATED SYNTHETIC COMPOSITIONS AND METHOD OF USING SAME

This application is a continuation of 08/947,055 filed Oct. 8, 1997 now U.S. Pat. No. 6,149,947 which is a continuation of 08/596,689 filed Feb. 2, 1996 abandon which is a continuation of 08/334,795 filed Nov. 4, 1994 abandon which is a continuation of 09/975,071 filed Nov. 6, 1992 abandon.

BACKGROUND OF THE INVENTION

This application relates to compositions of aqueous oak bark extract, to synthetic compositions containing the key active ingredients of oak bark extract and to the use of such compositions in the treatment of skin cancer and other skin disorders.

Oak bark extract has been described in U.S. Pat. No. 5,080,900 which is incorporated herein by reference, for use in the treatment of skin ulcers, particularly decubitus ulcers or bed sores. This material in a base of WHITFIELD pharmaceutical ointment has also been sold under the trade name BENCELOK® for use in the treatment of minor skin irritations (Whitfield and Bencelok are trademarks for pharmaceutical ointments). The amount of oak bark extract in these materials was relatively low, however. For example, the BENCELOK® preparations have continued from 0.25 to 3% by weight of ash-derived components based upon the total weight of the preparation.

SUMMARY OF THE INVENTION

It has now been found that higher concentrations of oak bark extract possess highly useful properties for the treatment of skin cancers, and that lower concentrations of oak bark extract possess additional therapeutic properties not heretofore recognized. For example, preparations containing 40–80% oak bark extract are useful in the treatment of acute cancerous skin ulcers. In addition, it has now been found that synthetic mixtures containing potassium ions, zinc ions, calcium ions provide many of the same advantageous properties of oak bark extract. The inclusion of rubidium ions and sulfate ions is also advantageous for some applications.

DETAILED DESCRIPTION OF THE INVENTION

Oak bark extract for use in the present invention is prepared from oak bark ash. The bark utilized can be from Red Oak (*Quercus rupra* L), Black Oak (*Quercus velutina* Lam.), Shumerd Oak (*Quercus shumardi* i Buckl.), Scarlet Oak (*Quercus coccinea* Muenchb.), Willow oak (*Quercus phellos* L.) and other species of the Erythrobalanus group. The oak bark is burned to convert it into an ash, which is cooled and screened to provide a powder.

The ash powder is then poured slowly into boiling water and boiled, with stirring, for a period of time (1.5 to 4 hours) to achieve an intermediate oak bark extract. The hot intermediate extract is then filtered to recover a clear filtrate and boiled for an additional period of time to achieve the desired final concentration of oak bark extract. During this boiling step, a white precipitate forms which is separated from the oak bark extract and discarded. Table 1 shows processing conditions which can be used to prepare oak bark extract of various final concentrations. The solution concentrations are expressed as weight percent of oak bark ash derived material.

The oak bark extracts in accordance with the invention are complex mixtures of inorganic materials. Further, as is evident from the results of elemental analysis on the various solutions, (See Table 2) the relative amounts of the constituents vary from one concentration to another. For example, the 40% solutions (i.e., a solutions containing a total of 40% by weight of extracted oak bark materials and 60% by weight water) was found to be highly enriched in rubidium relative to lower concentration solutions.

The therapeutic activity of various constituents of oak bark extract has been analyzed with the result that silicon, strontium, barium, manganese, gallium, zirconium and titanium appear to be unnecessary, while therapeutic efficacy has been found for compositions containing just potassium, zinc and calcium ions, in combination with suitable counterions. Thus, synthetic formulations containing, by weight of inorganic solids, 10 to 80 parts potassium ions, preferably 30 to 50 parts 0.00001 to 20 parts zinc ions, preferably 1 to 10 parts

TABLE I

| Solution (%) | Temperature (° C.) | Processing Time (Hours) |
| --- | --- | --- |
| 0.25 | 98 ± 2 | 1.00 |
| 1.00 | 98 ± 2 | 2.00 |
| 10.00 | 98 ± 2 | 8.00 |
| 20.50 | 98 ± 2 | 12.00 |
| 40.00 | 98 ± 2 | 18.00 |
| 80.00 | 98 ± 2 | 21.00 |

0.01 to 10 parts calcium ions, preferably 1 to 5 parts 0 to 40 parts rubidium ions, preferably 1 to 30 parts, and 0 to 5 parts sulfur, in the form of elemental sulfur or sulfate, together with pharmaceutically acceptable counterions (e.g., $Cl^-$, $SO_4^=$, $CO_3^=$, $OH^-$, $Br^-$). The solution may also contain other inorganic cations, for example, up to 10 parts by weight of inorganic solids of cobalt, copper, iron, manganese, nickel, strontium or aluminum ions, preferably up to 1 part by weight. Further, the composition may include a pharmaceutically acceptable carrier such a water or an ointment or cream base which will result in a therapeutic composition having a pH of from 4 to 7, preferably pH 4.5 to 5.5.

Oak bark extract or the synthetic mixtures of the invention have been found to provide a variety of beneficial therapeutic properties. The therapeutic applications and the concentration of oak bark extract or synthetic mixture by weight of solids are summarized in Table 3.

TABLE 2

| | CONCENTRATION OF OAK BARK EXTRACT | | | | |
| --- | --- | --- | --- | --- | --- |
| Element | 0.25% | 1.00% | 10.00% | 20.50% | 40.00% |
| Hydrogen | 13.77% | 12.07 | 12.15% | 11.00% | 10.11% |
| Oxygen | 86.22% | 87.91 | 85.55% | 84.40% | 64.45% |

TABLE 2-continued

CONCENTRATION OF OAK BARK EXTRACT

| Element | 0.25% | 1.00% | 10.00% | 20.50% | 40.00% |
|---|---|---|---|---|---|
| Potassium | 43541 ppm | 0.01% | 2.10% | 4.50% | 25.15% |
| Bromine | 0.05 ppm | 0.07 ppm | 2.00 ppm | 2.02 ppm | 2.02 ppm |
| Calcium | 13.43 ppm | 35.67 ppm | 99.45 ppm | 208.72 ppm | 1000.43 ppm |
| Chlorine | 24.87 ppm | 45.11 ppm | 92.50 ppm | 185.31 ppm | 235.2 ppm |
| Chromium | 0.23 ppm | 0.55 ppm | 1.01 ppm | 0.49 ppm | 1000.12 ppm |
| Cobalt | ND | ND | 0.08 ppm | 0.16 ppm | 0.29 ppm |
| Copper | ND | ND | 0.11 ppm | 0.33 ppm | 0.68 ppm |
| Iron | ND | ND | 0.85 ppm | 1.70 ppm | 2.12 ppm |
| Lead | ND | ND | 0.23 ppm | 0.56 ppm | 0.3 ppm |
| Manganese | ND | ND | 0.04 ppm | 0.07 ppm | 0.07 ppm |
| Nickel | ND | ND | 0.33 ppm | 0.66 ppm | 2.11 ppm |
| Rubidium | 17.25 ppm | 42.79 ppm | 110.13 ppm | 220.60 ppm | 1320.23 ppm |
| Strontium | ND | 0.01 ppm | 1.79 ppm | 2.99 ppm | 3.3 ppm |
| Sulfur | 5.45 ppm | 30.01 ppm | 180.01 ppm | 373.40 ppm | 421.3 ppm |
| Titanium | 0.81 ppm | 0.24 ppm | 1.79 ppm | 3.44 ppm | 0.1 ppm |
| Zinc | 1.74 ppm | 4.78 ppm | 8.81 ppm | 17.65 ppm | 12.3 ppm |

ND: not detectable.

TABLE III

| Weight % of Oak Bark Extract | Indications |
|---|---|
| 0.25% | Fungal infection, minor infection, insect bites |
| 1.00% | Eczema, minor burns, sunburn, poison oak, poison ivy, poison sumac, wound healing |
| 3.00% | Pyodermas, dermatitis, pruritic dermatoses, eczema, minor burns, sunburn, poison oak, poison ivy, poison sumac, decubitus ulcers, tropical ulcers, wound healing |
| 5.00% | Decubitus, psoriasis |
| 10.00% | Psoriasis, impetigo, Kaposi sarcoma, warts, gangrene, ischemic ulcer, keratosis |
| 20.50% | Precancerous lesions, basal cell epithelioma, squamous cell carcinoma, keratoacanthoma |
| 40.00% | Acute cancerous ulcers |
| 80.00% | Acute cancerous ulcers |

In particular, compositions containing about 20% or more, preferably 30% to 80% and more preferably 40% to 80%, of oak bark extract or a similarly concentrated synthetic mixture according to the invention can be used to treat cancerous and precancerous skin lesions. As used herein, the term cancerous and precancerous skin lesions includes but is not limited to basal cell epithelioma, squamous cell carcinoma, keratoacanthoma.

Compositions according to the invention are also useful for treating abrasions and other partial thickness wounds. Useful compositions include at least potassium, zinc and calcium ions and may include other ionic components as well as described in Examples 1 and 2. The composition is advantageously applied in a cream or ointment base over a period of several days. Similar compositions were found to be useful in the treatment of gangrene, impetigo, psoriasis, although longer periods of treatment may be required.

While not intending to be bound by any particular mechanism of action, it appears that oak bark extract and synthetic mixtures containing the key ingredients of oak bark extract function to enhance wound healing by providing complexing ions which interact with enzymes such as alkaline phosphatase, carbonic anhydrase, carboxypeptidase, various enhydrogenases, arginase, carnosinase, dehydropeptidase, glycine dipeptidase, histidine deaminase and tripeptidase, oxyloacetic carboxylase, and some lecithinases and enolases. These enzymes are involved in numerous biosynthetic pathways necessary for wound healing, for example, collagen biosynthesis, and are believed to function with greater efficiency in the presence of the complexing ions.

The application will now be further described by way of the following, non-limiting examples.

EXAMPLE 1

A synthetic mixture was prepared by combining potassium sulfate (7.50 g), potassium hydroxide (7.65 g), calcium hydroxide (0.05 g), iron sulfate (0.4 mg), cobaltous bromide (0.1 mg), copper chloride (0.3 mg), zinc sulfate (1.2 mg), strontium chloride (0.3 mg) and rubidium sulfate (0.13 mg) in distilled water (59.09 g) and WHITFIELD ointment (433.57 g). The total amount of synthetic chemicals was 3% in weight. The ointment was applied twice daily to three patients with severe abrasion. Prior to treatment, abrasions were cleaned with rubbing alcohol. All patients showed disappearance of abrasion within five days of treatments.

EXAMPLE 2

A synthetic mixture was prepared by combining zinc oxide (2.5 g), calcium hydroxide (2 g), potassium carbonate (3.5 g) and potassium hydroxide (12 g) in distilled water (80 g) and WHITFIELD ointment (57 g). The total amount of synthetic chemicals was 3% in weight. This formulation was used to treat an outpatient with a severe abrasion on his left arm. The abrasion was cleaned with rubbing alcohol to remove any contamination. The ointment was applied to abrasion twice daily. The abrasion healed within 72 hours.

EXAMPLE 3

A synthetic mixture was prepared by combining zinc sulfate (2.5 g), calcium hydroxide (2 g), potassium carbonate (3.5 g) and potassium hydroxide (12 g) in distilled water (80 g) and WHITFIELD ointment (57 g). The total amount of synthetic chemicals was 3% in weight. This formulation was used to treat an outpatient with venous stasis. The venous stasis was cleaned with a 3% solution of hydrogen peroxide and pad dried. The ointment was applied to venous stasis twice daily. Reduction in ulcer size 60–70% within 72 hours was observed. Complete granulation within days for ulcers less than 2 cm; 7 days for ulcers less than 4 cm.

EXAMPLE 4

A synthetic mixture was prepared by combining zinc sulfate (2.5 g), calcium hydroxide (2 g), potassium carbonate (3.5 g) and rubidium hydroxide (6 g), potassium hydroxide (6 g) in distilled water (80 g) and WHITFIELD ointment (57 g). The total amount of synthetic chemicals was 3% in weight. This formulation was used to treat an outpatient with laceration. The laceration was cleaned with rubbing alcohol and air dried. The ointment was applied to the laceration twice daily. The laceration reduced its redness with 4 hours and healed with 72 hours.

EXAMPLE 5

A synthetic mixture was prepared by combining potassium hydroxide (6.6 g), rubidium hydroxide (0.4 g), zinc sulfate (0.6 g), sulfur (2 g) and calcium hydroxide (0.1 g) in distilled water (14.55 g) and WHITFIELD ointment (72.75 g). The total amount of synthetic chemicals was 10% in weight. This formulation was used to treat an outpatient with psoriasis in the right arm and right leg. The psoriasis was cleaned with rubbing alcohol to remove any contamination. The ointment was applied to abrasion twice daily. The psoriasis healed in six weeks.

EXAMPLE 6

A synthetic mixture was prepared by combining potassium hydroxide (6.6 g), rubidium hydroxide (0.4 g), zinc sulfate (0.6 g), sulfur (2 g) and calcium hydroxide (0.1 g) in distilled water (14.55 g) and WHITFIELD ointment (72.75 g). The total amount of synthetic chemicals was 10% in weight. This formulation was used to treat an outpatient with impetigo at the back. The back was thoroughly cleaned with rubbing alcohol to remove any contamination. The ointment was applied to impetigo twice daily. The impetigo healed in four weeks.

EXAMPLE 7

A synthetic mixture was prepared by combining potassium hydroxide (6.6 g), rubidium hydroxide (0.4 g), zinc sulfate (0.6 g), sulfur (2 g) and calcium hydroxide (0.1 g) in distilled water (14.55 g) and WHITFIELD ointment (72.75 g). The total amount of synthetic chemicals was 10% in weight. This formulation was used to treat an outpatient with gangrene in his feet. The gangrene was thoroughly cleaned with hydrogen peroxide to remove any contamination. The ointment was applied to gangrene twice daily. The gangrene healed in six weeks.

EXAMPLE 8

A polyethylene-glycol based ointment (105 g) with 10% oak bark extract was prepared from red oak bark extract (20.5%, 100 g) to treat pustules on a patient's face and neck. The pustules were cleaned with a 3% saline solution. The ointment was then applied to the pustules. After 12 hours of treatment, the "angry red" face began to fade; after 20 hours, the face began to turn normal. The pustules never reoccurred.

EXAMPLE 9

An aqueous solution containing 80% red oak bark by weight was prepared in accordance with the conditions outlined in Table 1. The solution was used to treat a patient with melanoma in the front of his left ear. The size of the tumor was as big as a thumbnail. At the top of it was a crusty brown. The therapy included removal of the exudate by washing the lesions with soap and water and pad dried. The solution was applied twice daily to the melanoma. After two weeks of treatments, the tumor started to clear up; and after an additional two weeks of treatments, the melanoma completely disappeared, leaving only a clean, white-looking spot.

EXAMPLE 10

A polyethylene glycol-based ointment (33.33 g) with 30% oak bark extract was prepared from red oak bark extract (40.0%, 100 g) to treat venous stasis of a woman. The venous stasis was cleaned with rubbing alcohol. Air dried. The ointment was applied twice daily over a period of four days, the swelling reduced and the pain subsided.

EXAMPLE 11

Two ointments with a concentration of 20% and 50% oak bark extract solution, respectively, were prepared by mixing the 80% red oak extract solution with salicylic acid, benzoic acid and polyethylene glycol. The 20% ointment contained 100 g red oak extract solution (80%), 103.20 g PEG3350, 156.03 g PEG400, 30.57 g benzoic acid and 10.20 g salicylic acid. The 50% ointment contained 100 g red oak extract solution (80%), 20.64 g PEG3350, 31.21 g PEG400, 6.11 g benzoic acid and 2.04 g salicylic acid. The 50% ointment was applied twice daily to a patient with Kaposi's sarcoma. Prior to application, open lesions were cleaned with 3% hydrogen peroxide. A wet dressing was used. The size of the sarcoma reduced to a diameter of an inch after one week of treatment. The 20% ointment was applied thereafter. The patient completely healed in 45 days of treatments.

EXAMPLE 12

An ointment with 3% oak bark extract was prepared by mixing 20.5% oak bark extract solution with salicylic acid (19.82 g), benzoic acid (59.41 g), PEG3350 (200.55 g) and PEG400 (303.22 g). The ointment was used to treat molds of a HIV-positive patient. Ointment was applied twice daily to molds directly. Within 3½ weeks, molds disappeared.

EXAMPLE 13

An ointment with 3% oak bark extract by weight was prepared, by mixing 20.5% oak bark extract solution with salicylic acid (19.82 g), benzoic acid (59.41 g), PEG3350 (200.55 g) and PEG400 (303.22 g). The ointment was used to treat molds of a HIV-positive patient. Ointment was applied twice daily to molds which were surgically clipped. The molds dried up within 48 hours.

EXAMPLE 14

A male with six Kaposi's lesions was treated with an ointment containing 100 g 8% oak bark extract solution and 156.25 g polyethylene glycol. Ointment was applied twice daily directly over lesions. Lesions with sizes larger than one inch reduced their sizes 60% after 36 days of treatments. Lesions with sizes less than one-half of an inch healed within a week of treatment.

EXAMPLE 15

A polyethylene glycol-based ointment (105 g) contained 10% oak bark extract by weight, prepared from 100 g of 20.5% red oak bark solution, was used to treat a patient suffering from actinic keratosis. The ointment was applied twice daily over a period of four months, by which time the lesions had disappeared.

EXAMPLE 16

Five additional synthetic compositions were prepared as follows:
(a) Potassium carbonate (10 g), rubidium hydroxide (4 g), zinc sulfate (2.5 g), calcium hydroxide (3.5 g), distilled water (80 g), WHITFIELD ointment (57 g).
(b) Potassium hydroxide (log), rubidium hydroxide (4 g), zinc sulfate (2.5 g), calcium hydroxide (3.5 g), distilled water (80 g), WHITFIELD ointment (57 g).
(c) Potassium carbonate (12 g), rubidium hydroxide (5.5 g), zinc oxide (2.5 g), distilled water (80 g), distilled water (80 g), WHITFIELD ointment (57 g).
(d) Potassium carbonate (12 g), rubidium hydroxide (5.5 g), zinc sulfate (2.5 g) distilled water (80 g), WHITFIELD ointment (57 g).
(e) Calcium hydroxide (12 g), rubidium hydroxide (5.5 g), zinc sulfate (2.5 g), distilled water (80 g), WHITFIELD ointment (57 g).

We claim:

1. A method for enhancing wound healing at a wound site comprising applying an effective amount of a therapeutic composition comprising:
   a pharmaceutically acceptable carrier; and
   an active ingredient of inorganic solids comprising 10–80 parts by weight of potassium ions, 0.00001–20 parts by weight of zinc ions, 0.01–10 parts by weight of calcium ions and rubidium ions in an amount of up to 40 parts by weight, said parts by weight being expressed as parts by weight of inorganic solids.

2. The method of claim 1, wherein said carrier is water.

3. The method of claim 1, wherein said carrier is cream based.

* * * * *